United States Patent
Viola

(10) Patent No.: US 8,342,380 B2
(45) Date of Patent: *Jan. 1, 2013

(54) VARIABLE COMPRESSION SURGICAL FASTENER APPARATUS

(75) Inventor: Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/465,251

(22) Filed: May 7, 2012

(65) Prior Publication Data

US 2012/0228359 A1 Sep. 13, 2012

Related U.S. Application Data

(63) Continuation of application No. 12/417,709, filed on Apr. 3, 2009, now Pat. No. 8,186,556.

(60) Provisional application No. 61/051,911, filed on May 9, 2008.

(51) Int. Cl.
*A61B 17/04* (2006.01)
*A61B 17/10* (2006.01)

(52) U.S. Cl. .................. 227/178.1; 227/177.1; 606/142

(58) Field of Classification Search .... 227/175.1–182.1; 606/142

See application file for complete search history.

(56) References Cited

U.S. PATENT DOCUMENTS

| | | | |
|---|---|---|---|
| 1,756,670 A | 4/1930 | Treat | |
| 3,079,606 A | 3/1963 | Boris et al. | |
| 3,258,012 A | 6/1966 | Nakayama et al. | |
| 3,744,495 A | 7/1973 | Johnson | |
| 3,771,526 A | 11/1973 | Rudie | |
| 3,837,555 A | 9/1974 | Green | |
| 4,014,492 A | 3/1977 | Rothfuss | |
| 4,278,091 A | 7/1981 | Borzone | |
| 4,319,576 A | 3/1982 | Rothfuss | |
| 4,475,679 A | 10/1984 | Fleury, Jr. | |
| 4,527,437 A | 7/1985 | Wells | |
| 4,531,522 A | 7/1985 | Bedi et al. | |
| 4,532,927 A | 8/1985 | Miksza, Jr. | |
| 4,548,202 A | 10/1985 | Duncan | |
| 4,573,469 A | 3/1986 | Golden et al. | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,627,437 A | 12/1986 | Bedi et al. | |

(Continued)

FOREIGN PATENT DOCUMENTS

EP 0 129 442 12/1984

(Continued)

OTHER PUBLICATIONS

European Search Report EP06 01 6963.8-2318 dated Mar. 9, 2007.

(Continued)

*Primary Examiner* — Robert Long

(57) ABSTRACT

A surgical fastener applying apparatus includes an anvil section and a cartridge section, where the cartridge section and the anvil section are movable from an unclamped position to a clamped position. The cartridge section has a plurality of retention slots, a plurality of first surgical fasteners and a plurality of second surgical fasteners. The plurality of first surgical fasteners has a first backspan with a first configuration and the plurality of second surgical fasteners has a second backspan with a second different configuration. In addition, when the first configuration applies a first compressive force to tissue and the second configuration applies a second different compressive force to tissue.

10 Claims, 8 Drawing Sheets

U.S. PATENT DOCUMENTS

| | | | |
|---|---|---|---|
| 4,741,336 A | 5/1988 | Failla et al. | |
| 4,767,044 A | 8/1988 | Green | |
| 4,809,695 A | 3/1989 | Gwathmey et al. | |
| 4,848,637 A | 7/1989 | Pruitt | |
| 4,881,545 A | 11/1989 | Isaacs et al. | |
| 4,930,503 A | 6/1990 | Pruitt | |
| 4,941,623 A | 7/1990 | Pruitt | |
| 4,978,049 A | 12/1990 | Green | |
| 5,027,834 A | 7/1991 | Pruitt | |
| 5,108,422 A | 4/1992 | Green et al. | |
| 5,180,092 A | 1/1993 | Crainich | |
| 5,201,746 A | 4/1993 | Shichman | |
| 5,209,756 A | 5/1993 | Seedhom et al. | |
| 5,219,353 A | 6/1993 | Garvey, III et al. | |
| 5,240,163 A | 8/1993 | Stein et al. | |
| 5,282,829 A | 2/1994 | Hermes | |
| 5,342,396 A | 8/1994 | Cook | |
| 5,350,400 A | 9/1994 | Esposito et al. | |
| 5,352,229 A | 10/1994 | Goble et al. | |
| 5,425,489 A | 6/1995 | Shichman et al. | |
| 5,439,479 A | 8/1995 | Shichman et al. | |
| 5,441,193 A | 8/1995 | Gravener | |
| 5,452,836 A | 9/1995 | Huitema et al. | |
| 5,452,837 A | 9/1995 | Williamson, IV et al. | |
| 5,470,010 A * | 11/1995 | Rothfuss et al. | 227/177.1 |
| 5,484,095 A | 1/1996 | Green et al. | |
| 5,497,931 A | 3/1996 | Nakamura | |
| 5,501,693 A | 3/1996 | Gravener | |
| 5,509,920 A | 4/1996 | Phillips et al. | |
| 5,571,116 A | 11/1996 | Bolanos | |
| 5,571,285 A | 11/1996 | Chow et al. | |
| 5,584,856 A | 12/1996 | Jameel et al. | |
| 5,620,452 A | 4/1997 | Yoon | |
| 5,634,926 A | 6/1997 | Jobe | |
| 5,667,526 A | 9/1997 | Levin | |
| 5,667,527 A | 9/1997 | Cook | |
| 5,676,674 A | 10/1997 | Bolanos et al. | |
| 5,697,542 A | 12/1997 | Knodel et al. | |
| 5,709,680 A | 1/1998 | Yates et al. | |
| 5,741,268 A | 4/1998 | Schutz | |
| 5,810,822 A | 9/1998 | Mortier | |
| 5,865,361 A | 2/1999 | Milliman et al. | |
| 5,871,135 A | 2/1999 | Williamson, IV et al. | |
| 5,879,371 A | 3/1999 | Gardiner et al. | |
| 5,915,616 A | 6/1999 | Viola et al. | |
| 5,961,521 A | 10/1999 | Roger | |
| 5,964,394 A | 10/1999 | Robertson | |
| 6,083,242 A | 7/2000 | Cook | |
| 6,202,914 B1 | 3/2001 | Geiste et al. | |
| 6,273,897 B1 | 8/2001 | Dalessandro et al. | |
| 6,325,810 B1 | 12/2001 | Hamilton et al. | |
| 6,348,054 B1 | 2/2002 | Allen | |
| 6,702,826 B2 | 3/2004 | Liddicoat et al. | |
| 6,706,057 B1 | 3/2004 | Bidoia et al. | |
| 6,786,382 B1 | 9/2004 | Hoffman | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,001,411 B1 | 2/2006 | Dean | |
| 7,044,352 B2 | 5/2006 | Shelton, IV et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,147,140 B2 | 12/2006 | Wukusick et al. | |
| 7,377,928 B2 | 5/2008 | Zubik et al. | |
| 7,398,908 B2 | 7/2008 | Holsten et al. | |
| 7,407,076 B2 | 8/2008 | Racenet | |
| 7,455,676 B2 | 11/2008 | Holsten et al. | |
| 7,472,815 B2 | 1/2009 | Shelton et al. | |
| 7,500,979 B2 | 3/2009 | Hueil et al. | |
| 7,506,791 B2 | 3/2009 | Omaits et al. | |
| 7,547,312 B2 | 6/2009 | Bauman et al. | |
| 7,604,151 B2 | 10/2009 | Hess et al. | |
| 7,641,091 B2 | 1/2010 | Olson et al. | |
| 7,669,746 B2 | 3/2010 | Shelton, IV | |
| 7,794,475 B2 | 9/2010 | Hess et al. | |
| 7,926,691 B2 | 4/2011 | Viola et al. | |
| 8,186,556 B2 * | 5/2012 | Viola | 227/178.1 |
| 8,205,780 B2 * | 6/2012 | Sorrentino et al. | 227/176.1 |
| 2002/0177850 A1 | 11/2002 | Bremer | |
| 2004/0004105 A1 | 1/2004 | Jankowski | |
| 2004/0073222 A1 | 4/2004 | Koseki | |
| 2004/0232195 A1 | 11/2004 | Shelton et al. | |
| 2004/0232199 A1 | 11/2004 | Shelton et al. | |
| 2004/0247415 A1 | 12/2004 | Mangone, Jr. | |
| 2005/0006430 A1 | 1/2005 | Wales | |
| 2005/0006431 A1 | 1/2005 | Shelton et al. | |
| 2005/0006434 A1 | 1/2005 | Wales | |
| 2005/0023324 A1 | 2/2005 | Doll et al. | |
| 2005/0023325 A1 | 2/2005 | Gresham et al. | |
| 2005/0070925 A1 | 3/2005 | Shelton, IV et al. | |
| 2005/0070958 A1 | 3/2005 | Swayze et al. | |
| 2005/0139633 A1 | 6/2005 | Wukusick et al. | |
| 2005/0173490 A1 | 8/2005 | Shelton, IV | |
| 2005/0178813 A1 | 8/2005 | Swayze et al. | |
| 2005/0187576 A1 | 8/2005 | Whitman et al. | |
| 2005/0263562 A1 | 12/2005 | Shelton, IV et al. | |
| 2005/0267530 A1 | 12/2005 | Cummins | |
| 2006/0000868 A1 | 1/2006 | Shelton, IV et al. | |
| 2006/0015144 A1 | 1/2006 | Burbank et al. | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025810 A1 | 2/2006 | Shelton, IV | |
| 2006/0025811 A1 | 2/2006 | Shelton, IV | |
| 2006/0025812 A1 | 2/2006 | Shelton, IV | |
| 2006/0025813 A1 | 2/2006 | Shelton, IV et al. | |
| 2006/0025816 A1 | 2/2006 | Shelton, IV | |
| 2006/0025817 A1 | 2/2006 | Ortiz et al. | |
| 2006/0039779 A1 | 2/2006 | Ring | |
| 2006/0049230 A1 | 3/2006 | Shelton, IV et al. | |
| 2006/0085030 A1 | 4/2006 | Bettuchi et al. | |
| 2006/0097026 A1 | 5/2006 | Shelton, IV | |
| 2006/0124688 A1 | 6/2006 | Racenet et al. | |
| 2006/0163312 A1 | 7/2006 | Viola | |
| 2006/0226196 A1 | 10/2006 | Hueil et al. | |
| 2006/0291981 A1 | 12/2006 | Viola et al. | |
| 2007/0010838 A1 | 1/2007 | Shelton, IV et al. | |
| 2007/0034667 A1 | 2/2007 | Holsten et al. | |
| 2007/0131732 A1 | 6/2007 | Holsten et al. | |
| 2007/0262116 A1 | 11/2007 | Hueil et al. | |
| 2008/0041918 A1 | 2/2008 | Holsten et al. | |
| 2008/0078800 A1 | 4/2008 | Hess | |
| 2008/0078804 A1 | 4/2008 | Shelton et al. | |
| 2008/0082124 A1 | 4/2008 | Hess et al. | |
| 2009/0255975 A1 | 10/2009 | Zemlok et al. | |
| 2009/0255978 A1 | 10/2009 | Viola et al. | |
| 2009/0277948 A1 * | 11/2009 | Beardsley et al. | 227/178.1 |
| 2010/0237128 A1 * | 9/2010 | Miller et al. | 227/175.1 |
| 2011/0042439 A1 * | 2/2011 | Johnson et al. | 227/175.1 |
| 2011/0168760 A1 | 7/2011 | Viola et al. | |
| 2012/0145768 A1 * | 6/2012 | Sorrentino et al. | 227/181.1 |

FOREIGN PATENT DOCUMENTS

| | | |
|---|---|---|
| EP | 0129442 | 12/1984 |
| EP | 0 169 044 | 1/1986 |
| EP | 0169044 | 1/1986 |
| EP | 0588081 | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1607048 | 12/2005 |
| EP | 1728473 | 12/2006 |
| EP | 1 754 445 | 2/2007 |
| EP | 1754445 | 2/2007 |
| EP | 1 785 098 | 5/2007 |
| EP | 1785098 | 5/2007 |
| EP | 2 095 777 | 9/2009 |
| EP | 2095777 | 9/2009 |
| FR | 2838952 | 10/2003 |

| | | |
|---|---|---|
| GB | 2 019 296 | 10/1979 |
| GB | 2019296 | 10/1979 |
| GB | 2 029 754 | 3/1980 |
| GB | 2029754 | 3/1980 |
| GB | 2 051 287 | 1/1981 |
| GB | 2051287 | 1/1981 |
| SU | 405234 | 9/1975 |
| SU | 1333319 | 8/1987 |
| SU | 1442191 | 12/1988 |
| SU | 1459659 | 2/1989 |
| WO | WO86/02254 | 4/1986 |
| WO | WO 86/02254 | 4/1986 |
| WO | WO90/05489 | 5/1990 |
| WO | WO 90/05489 | 5/1990 |
| WO | WO 96/19146 | 6/1996 |
| WO | WO 97/34533 | 9/1997 |
| WO | WO97/34533 | 9/1997 |
| WO | WO 02/30296 | 4/2002 |
| WO | WO02/30296 | 4/2002 |
| WO | WO 03/094743 | 11/2003 |
| WO | WO03/094743 | 11/2003 |
| WO | WO03/094747 | 11/2003 |
| WO | WO 03/094747 | 11/2003 |
| WO | WO 2006/055385 | 5/2006 |
| WO | WO2006/055385 | 5/2006 |
| WO | WO2008/007377 | 1/2008 |
| WO | WO 2008/007377 | 1/2008 |
| WO | WO2008/003950 | 4/2008 |
| WO | WO 2008/039250 | 4/2008 |
| WO | WO 2008/089050 | 7/2008 |
| WO | WO2008/089050 | 7/2008 |

OTHER PUBLICATIONS

European Search Report EP07 25 4366 dated Nov. 11, 2010.
European Search Report EP08 25 2283 dated Jan. 15, 2009.
European Search Report EP09 25 1067 dated Mar. 17, 2011.
European Search Report EP09 25 1224.3-2310 dated Oct. 8, 2009.
European Search Report EP09 25 1268 dated Sep. 9, 2009.
European Search Report EP09 251793.7 dated Nov. 16, 2009.
European Search Report EP10 251797 dated Jan. 31, 2011.
European Search Report EP9251240.9 dated Oct. 19, 2009.
European Search Report for EP 06016963.8-2318 date of completion is Mar. 9, 2007.
European Search Report for EP 09251224.3-2310 date of completion is Sep. 1, 2009.
European Search Report dated Jan. 31, 2011 for European Patent Application No. EP 10 25 1797.
International Search Report from EP Application No. 07 25 4366 dated Nov. 11, 2010.
International Search Report from EP Application No. 09 25 1067 mailed Mar. 17, 2011.
European Search Report EP 08 25 2283 dated Jan. 15, 2009.
European Search Report EP 09 25 1268 dated Sep. 9, 2009.
European Search Report EP 09 251793.7 dated Nov. 16, 2009.
European Search Report EP 09 25 1240.9 dated Oct. 19, 2009.

* cited by examiner

VARIABLE COMPRESSION SURGICAL FASTENER APPARATUS

CROSS-REFERENCE TO RELATED APPLICATIONS

This application is a continuation of U.S. application Ser. No. 12/417,709 filed Apr. 3, 2009 now U.S. Pat. No. 8,186,556, which claims benefit of application No. 61/051,911 filed May 9, 2008, and the disclosures of each of the above-identified applications are hereby incorporated by reference in their entirety.

BACKGROUND

1. Technical Field

The present disclosure relates to surgical fastener applying apparatus. More particularly, the present disclosure relates to a surgical fastener cartridge that includes a plurality of surgical fasteners configured to apply varying compressive forces to tissue.

2. Background of the Related Art

Many varieties of surgical fastening apparatus are known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. Suitable examples of apparatus which may be used during the course of these procedures can be seen in U.S. Pat. Nos. 5,915,616; 6,202,914; 5,865,361; and 5,964,394.

In general, a surgical fastening apparatus will include an anvil that is approximated relative to a fastener cartridge during use. The anvil includes depressions that are aligned with, and/or are in registration with slots defined in the cartridge, through which the fasteners will emerge, to effectuate formation. Certain apparatus have fastener cartridges with one or more rows of fasteners disposed laterally or radially of a longitudinal slot that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners generally include a pair of legs adapted to penetrate tissue and connected by a backspan from which they extend. The staples are formed into a closed configuration, such as a "B" shaped configuration. Typically, the two-part fastener includes legs that are barbed and connected by a backspan which are engaged and locked into a separate retainer piece that is usually located in the anvil. In use, the two-part fastener is pressed into the tissue so that the barbs penetrate the tissue and emerge from the other side where they are then locked into the retainer piece. The retainers prevent the two-part fastener from dislodging from the tissue. The two-part fasteners are not intended to be unlocked or removable. They are generally made of a bioabsorbable material.

During each of the aforementioned surgical procedures, the tissue is initially gripped or clamped between the anvil and cartridge such that individual fasteners can be ejected from the cartridge, through the slots, and forced through the clamped tissue. Thereafter, the fasteners are formed by driving them into the depressions formed on the anvil.

A common concern in each of these procedures is hemostasis, or the cessation of bleeding of the target tissue. It is commonly known that by increasing the amount of pressure applied to a wound, the flow of blood can be limited, thereby decreasing the time necessary to achieve hemostasis. To this end, conventional surgical fastening apparatus generally apply two or more rows of fasteners about a cut-line to compress the surrounding tissue in an effort to stop any bleeding and to join the cut tissue together. Each of the fasteners will generally apply a compressive force to the tissue sufficient to effectuate hemostasis, however, if too much pressure is applied, this can result in a needless reduction in blood flow to the tissue surrounding the cut-line. Accordingly, too much pressure in the joining of tissue together may result in an elevated level of necrosis, a slower rate of healing, and/or a greater recovery period.

Consequently, it would be advantageous to provide a surgical fastening apparatus capable of limiting the flow of blood in the tissue to effectuate hemostasis and wound closure, while maximizing blood flow in the surrounding tissue to facilitate healing. Additionally, when tissue is clamped and compressed between the anvil and cartridge, differences in the tissue can mean that portions of the tissue are thicker than other portions of tissue. It would therefore be advantageous to provide staples which could better accommodate the different tissue thicknesses.

SUMMARY

The present disclosure is directed towards surgical stapling instruments configured to limit the flow of blood in tissue to effectuate hemostasis and wound closure, while maximizing blood flow in the surrounding tissue to facilitate healing. In particular, embodiments of the present disclosure include varying the formation of surgical fasteners in order to vary the compressive force that is applied to surrounding tissue. Further still, when the surgical fasteners are formed within tissue, recesses in the backspans of the surgical fasteners cooperate with the legs of the surgical fasteners to apply a compressive force to surrounding tissue, whereby a varying of the recesses corresponds to a varying of the compressive forces applied to surrounding tissue.

A fastener assembly is disclosed herein for a surgical instrument including a cartridge section and an anvil section, wherein the cartridge section and the anvil section are movable from an unclamped position to a clamped position to clamp tissue therebetween. The cartridge section has a plurality of retention slots disposed therein. In addition, a plurality of first surgical fasteners and a plurality of second surgical fasteners are disclosed, wherein each surgical fastener is disposed within a corresponding retention slot.

According to one aspect of the disclosure, the surgical fastener applying apparatus includes the plurality of first surgical fasteners having a first backspan with a first configuration and the plurality of second surgical fasteners having a second backspan with a second configuration. According to this embodiment, the first configuration is different from the second configuration. The first configuration is configured to apply a first compressive force to tissue upon formation of the plurality of the first surgical fasteners and the second configuration is configured to apply a second compressive force to tissue upon formation of the plurality of second surgical fasteners. According to this embodiment, the second compressive force is different from the first compressive force.

In one embodiment, when the plurality of first surgical fasteners is formed, a plurality of first pushers disposed within the retention slots may form a recess in the first backspan of the first surgical fasteners to define the first configuration. In addition, when the plurality of second surgical fasteners are formed, a plurality of second pushers disposed within the retention slots may form a recess in the second backspan of the second surgical fasteners to define the second configuration. The first recess may be different from the second recess. Further, as the anvil section and the cartridge section move from the unclamped position to the clamped position, the pressure applied to surrounding tissue may correspond to the size of the recess in the corresponding surgical fastener. Further still, the plurality of first pushers and the plurality of second pushers may form the corresponding recess in the corresponding backspan of the surgical fasteners at essentially the same time the surgical fasteners are driven against the anvil section.

According to another aspect of the present disclosure, the surgical fastener applying apparatus includes an actuation sled that is capable of moving distally through the cartridge section. The actuation sled may include at least one cam wedge. In addition, as the actuation sled travels distally through the cartridge, the cam wedge is capable of driving the pushers in order to deploy the surgical fasteners and drive them against the anvil section.

In another aspect of the present disclosure, the cartridge section includes a longitudinal slot configured to allow longitudinal movement of a knife bar therethrough. The cartridge section can also include a first inner row of retention slots and a first outer row of retention slots on a first side of the longitudinal slot, and a second inner row of retention slots and a second outer row of retention slots on a second side of the longitudinal slot, wherein each retention slot is aligned with a corresponding pusher and surgical fastener. In addition, the surgical fasteners in the first inner row and the second inner row can be formed with a bigger recess as compared to the surgical fasteners in the first outer row and the second outer row. Accordingly, there would be a smaller interior space within the surgical fasteners of the inner rows as compared to the outer rows of surgical fasteners. Moreover, a greater force would thus be applied to the tissue surrounding the inner rows as compared to the tissue surrounding the outer rows of surgical fasteners.

In another embodiment, the actuation sled can include a first inner cam wedge, a second inner cam wedge, a first outer cam wedge, and a second outer cam wedge, wherein the first inner wedge contacts the pushers in the first inner row of retention slots, the second inner cam wedge contacts the pushers in the second inner row of retention slots, the first outer cam wedge contacts the pushers in the first outer row of retention slots, and the second outer cam wedge contacts the pushers in the second outer row of retention slots.

BRIEF DESCRIPTION OF THE DRAWINGS

Various embodiments of the present disclosure are described hereinbelow with references to the drawings, wherein.

DETAILED DESCRIPTION OF EXEMPLARY EMBODIMENTS

Figure 1:
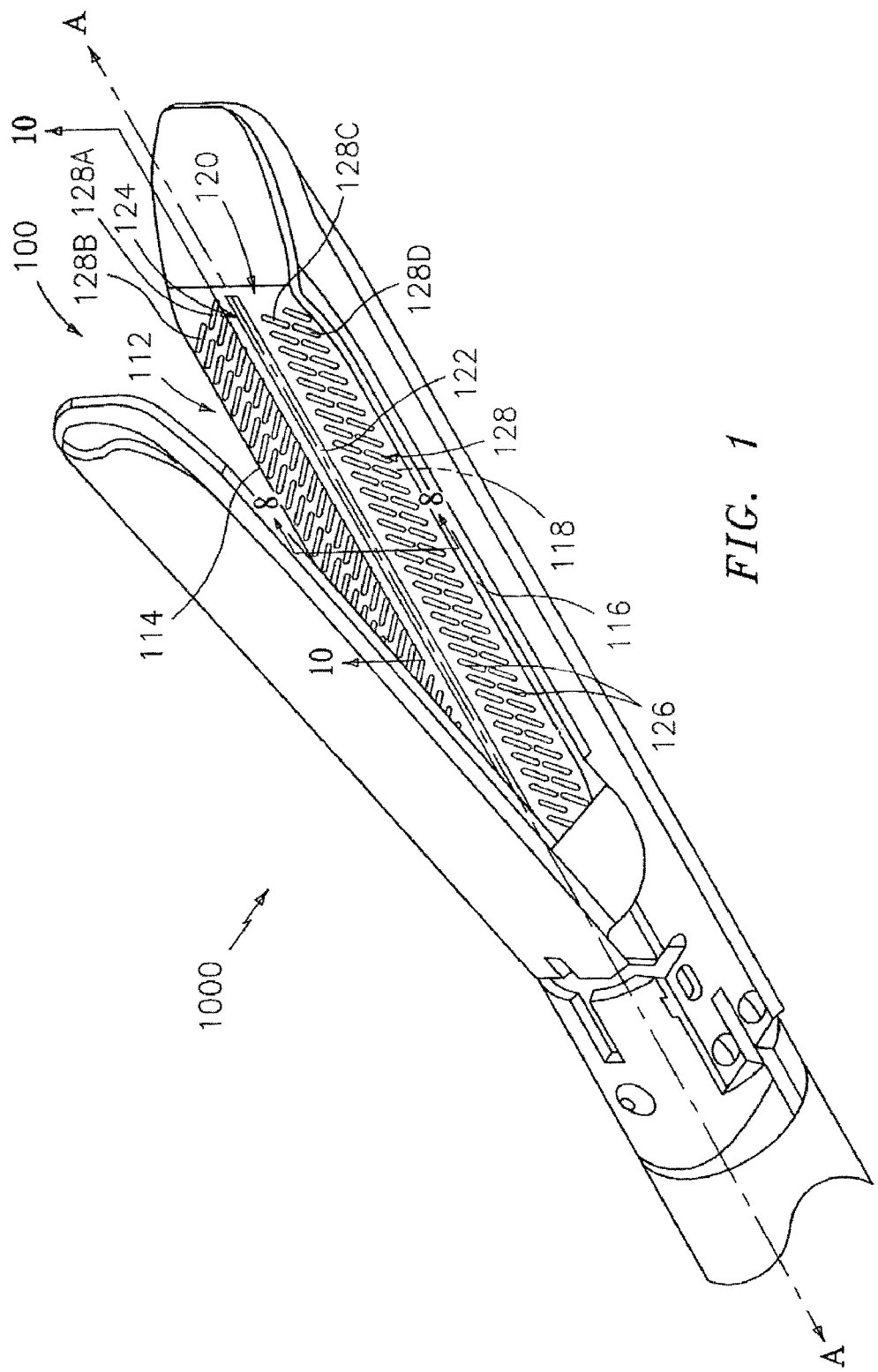
FIG. 1 is a top, perspective view of a distal end portion of a surgical fastener applying apparatus including a surgical fastener cartridge in accordance with an embodiment of the present disclosure.

Various exemplary embodiments of the presently disclosed surgical fastener cartridge will now be described in detail with reference to the drawings wherein like references numerals identify similar or identical elements. In the drawings and in the description which follows, the term "proximal" will refer to the end of the surgical fastener cartridge that is closer to the operator during use, while the term "distal" will refer to the end of the fastener cartridge that is further from the operator, as is traditional and conventional in the art. In addition, the term "surgical fastener" should be understood to include any substantially rigid structure formed of a biocompatible material that is suitable for the intended purpose of joining tissue together, including but not being limited to surgical staples, clips, and the like. The surgical fastener can be made of any biocompatible metal, such as titanium or stainless steel, or any biocompatible polymer, including absorbable or resorbable polymers.

Figure 7:
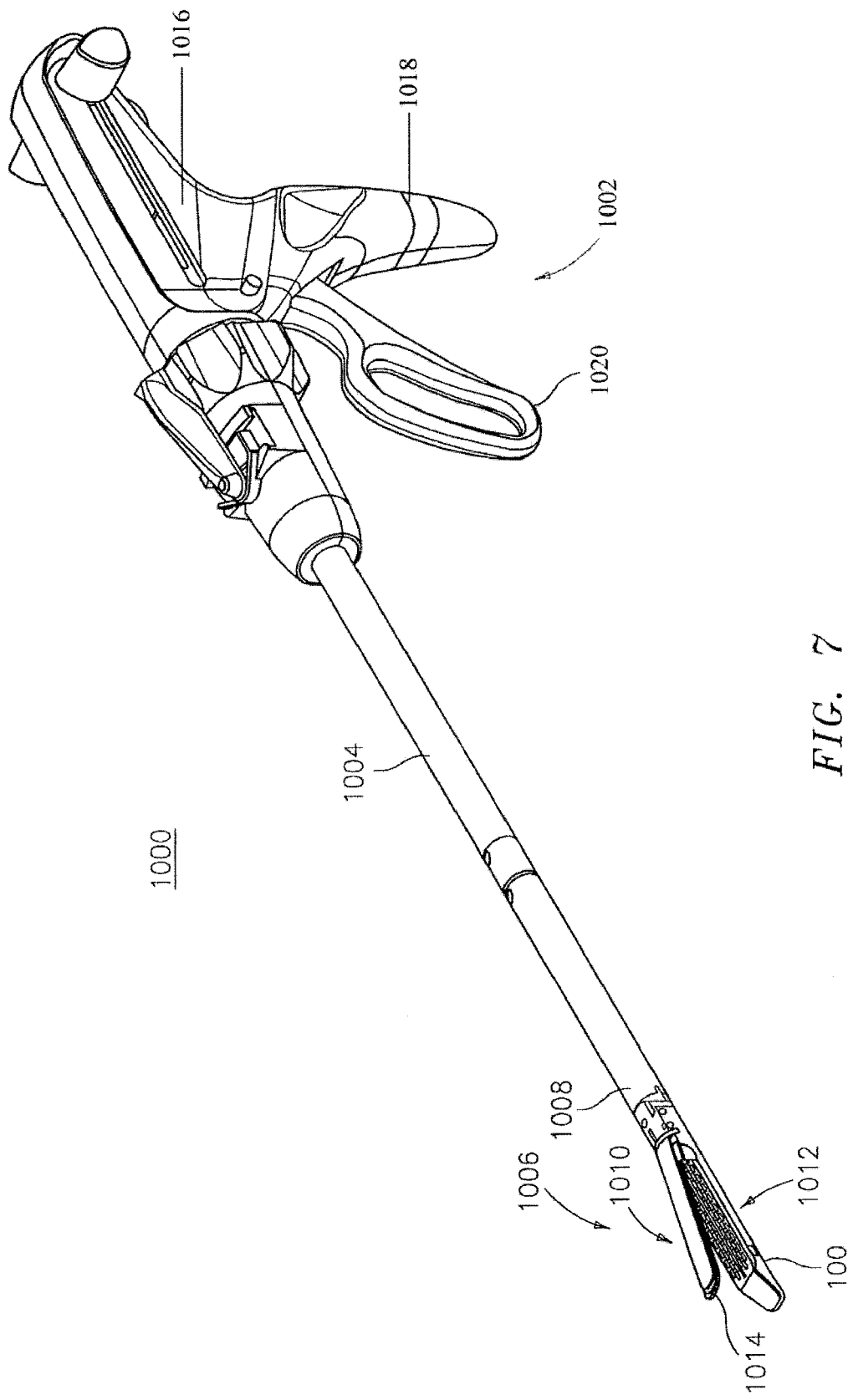
FIG. 7 is a perspective view of an exemplary surgical fastener applying apparatus in accordance with an embodiment of the present disclosure for use during a laparoscopic surgical procedure.

With reference to FIGS. 1 and 7, the surgical fastener applying apparatus 1000 according to an embodiment of the present disclosure will be discussed. Surgical fastener applying apparatus 1000 is used to sequentially apply a plurality of surgical fasteners, e.g., surgical fasteners 130 to a patient's tissue, and may be of the re-usable or disposable variety. Surgical fastener applying apparatus 1000 includes a handle 1002, an elongated shaft 1004 extending distally therefrom, and an operative tool 1006 coupled to a distal end 1008 of the elongated shaft 1004. (FIG. 7) The movable handle 1002 advances a drive rod distally to operate the operative tool 1006. However, other handles may be used such as, for example, motor-driven, hydraulic, ratcheting, etc. In general, operative tool 1006 is adapted to clamp, sequentially fasten together, and sever adjacent tissue segments along a cut-line. Accordingly, operative tool 1006 includes a pair of opposed jaws 1010, 1012 pivotally coupled with respect to one another and respectively including an anvil member 1014 and a surgical fastener cartridge 100.

In operation, surgical fastener applying apparatus 1000 is fired similarly to and in accordance with other known surgical stapling instruments. For a detailed discussion of the approximation and firing of surgical stapling instrument 1000, reference is made to commonly assigned U.S. Pat. No. 5,865,361, currently assigned to Tyco Healthcare Group LP, the entire contents of which is hereby incorporated herein by reference. The handle assembly 1002 includes a housing 1016, which includes stationary handle member 1018. A movable handle 1020 is pivotably supported within the housing 1016 and is biased away from the stationary handle member 1018. Movement of the movable handle 1020 in the direction of the stationary handle member 1018 imparts a driving force to an actuation shaft within the housing 1016 causing it to advance linearly in a distal direction. The anvil member 1014 and the staple cartridge 100 are moved closer relative to each other and a force is transmitted to the ejectors or pushers positioned adjacent to surgical fasteners 130 disposed within slots of the staple cartridge 100 thereby ejecting the surgical fasteners 130 and driving the surgical fasteners 130 against a staple forming surface of the anvil member 1014.

Surgical fastener cartridge 100 extends along a longitudinal axis "A-A" and includes a cartridge body 112 with a pair of side walls 114, 116, a bottom wall 118, and a top wall 120. (FIG. 1) The cartridge body 112 includes a longitudinal slot 122 that is configured to accommodate longitudinal movement of a knife (not shown) or other cutting element such that tissue may be severed along a cut-line. The top wall 120 further includes a tissue engaging surface 124, e.g., for engaging the tissue to be cut, and a plurality of fastener retention slots 126 arranged perpendicularly, or generally transversely, with respect to the longitudinal axis A-A in a pattern that extends substantially the entire length of the cartridge 100. As shown in FIG. 1, a first inner row 128A of slots 126 and a first outer row 128B of slots are formed on a first side of the longitudinal slot 122 and, on an opposite side of the longitudinal slot 122, the cartridge 100 has a second inner row 128c of slots and a second outer row 128D of slots. While the cartridge 100 is depicted as including pairs of rows on either side of the longitudinal slot 122, additional rows of fastener retention slots 126 may be included in additional embodiments of the cartridge 100. Cartridge 100 in preferred embodiments is removable and replaceable with another loaded cartridge, or forms part of a removable and replaceable loading unit.

Figure 2:
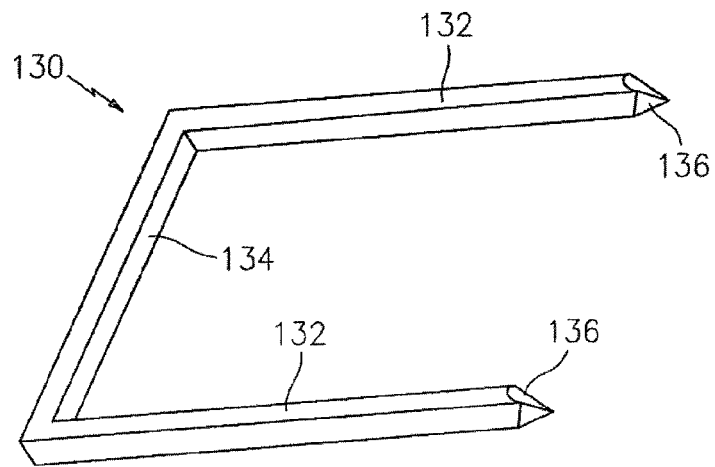
FIG. 2 is a side, perspective view of one embodiment of a surgical fastener, including a substantially linear backspan, shown prior to formation, for use with the surgical fastener cartridge of FIG. 1.

Each of the fastener retention slots 126 is configured to receive one of a plurality of surgical fasteners and pushers therein such that the surgical fasteners are deployed in rows, on opposite sides of the-cut-line created in the tissue during fastening. The initial configuration of the surgical fasteners is as shown in FIG. 2, or any other generally open configuration. The surgical fastener has a backspan and a pair of legs extending generally perpendicularly from the backspan such as, for example, surgical fastener 130 having backspan 134 and legs 132. The dimensions of the backspan 134 and the legs 132 can be varied such that the surgical fastener 130 may be used to fasten adjacent tissue segments "T1", "T2" of any thickness. (See FIG. 3*a*).

Figure 5B:
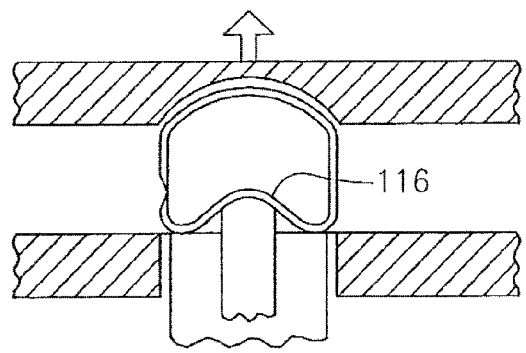
FIG. 5b is a partial cross-sectional view of a surgical fastening apparatus according to an embodiment of the present disclosure.
Figure 5A:
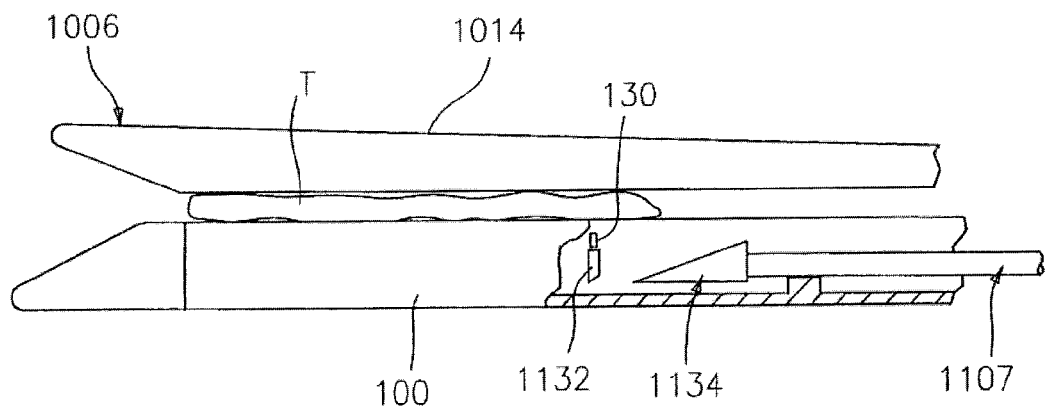
FIG. 5a is a partial cross-sectional view of a surgical fastening apparatus according to an embodiment of the present disclosure.
Figure 5C:
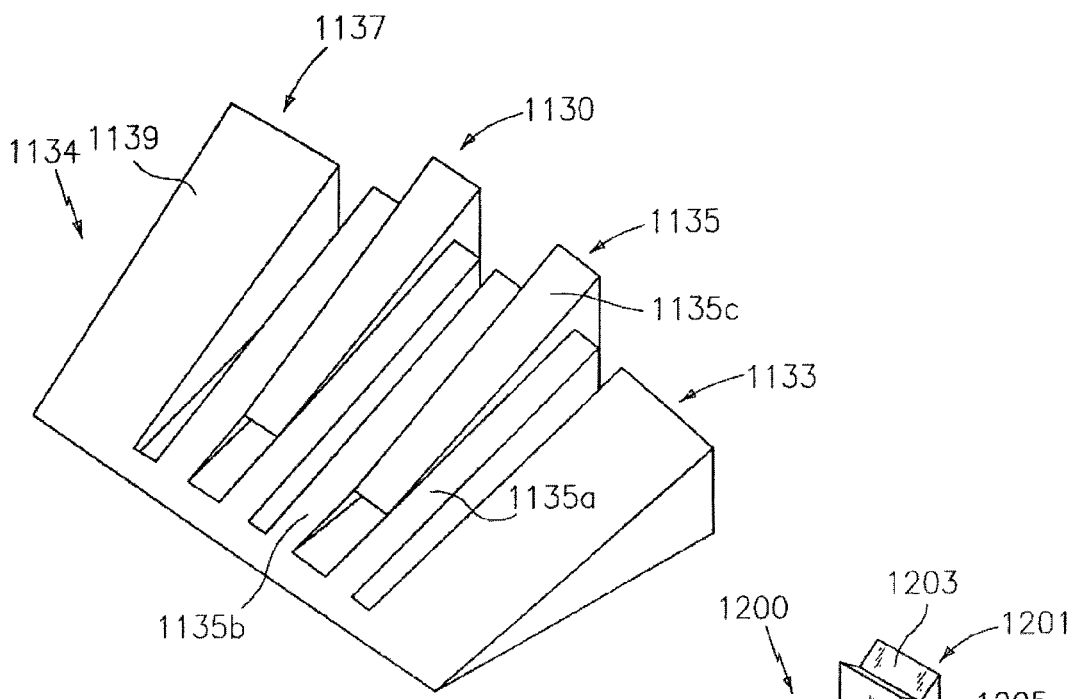
FIG. 5c is a perspective view of an actuation sled in accordance with an embodiment of the present disclosure.

The cartridge 100 includes an actuation sled 1134 that translates distally through the cartridge 100. The actuation sled 1134 is driven distally by a drive bar 1107, as shown in FIG. 5*a*, that is actuated by the handle 1002. The sled 1134 includes cam wedges that contact the pushers 1131 and drive the pushers 1132 upwardly to deploy the surgical fasteners 130 and drive them against the anvil member 1014. (FIG. 5*c*) In certain embodiments, the cartridge 100 has a sled 1134 with a first inner wedge 1135, a second inner wedge 1130, a first outer wedge 1133, and a second outer wedge 1137. The first inner wedge 1135 contacts the pushers in the first inner row 128A of fastener retention slots 126, the second inner wedge contacts the pushers in the second inner row 128C of retention slots 126, the first outer wedge contacts the pushers in the first outer row 128B of retention slots 126, and the second outer wedge contacts the pushers in the second outer row 128D of retention slots 126. The cam wedges 1135 are integrally formed with one another, or attached to one another, as shown in FIG. 5*c*.

Figure 3A:
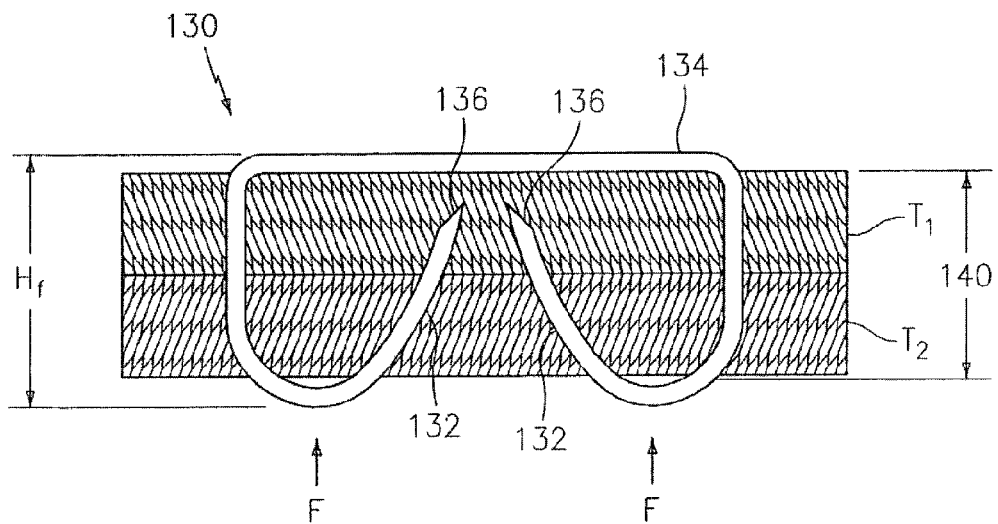
FIG. 3a is a cross-sectional view of a first surgical fastener subsequent to formation and within adjacent tissue segments.
Figure 3C:
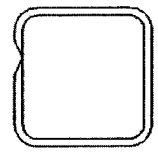
FIG. 3c is a cross-sectional view of a third surgical fastener subsequent to formation.
Figure 3B:
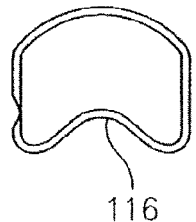
FIG. 3b is a cross-sectional view of a second surgical fastener subsequent to formation.
Figure 6:
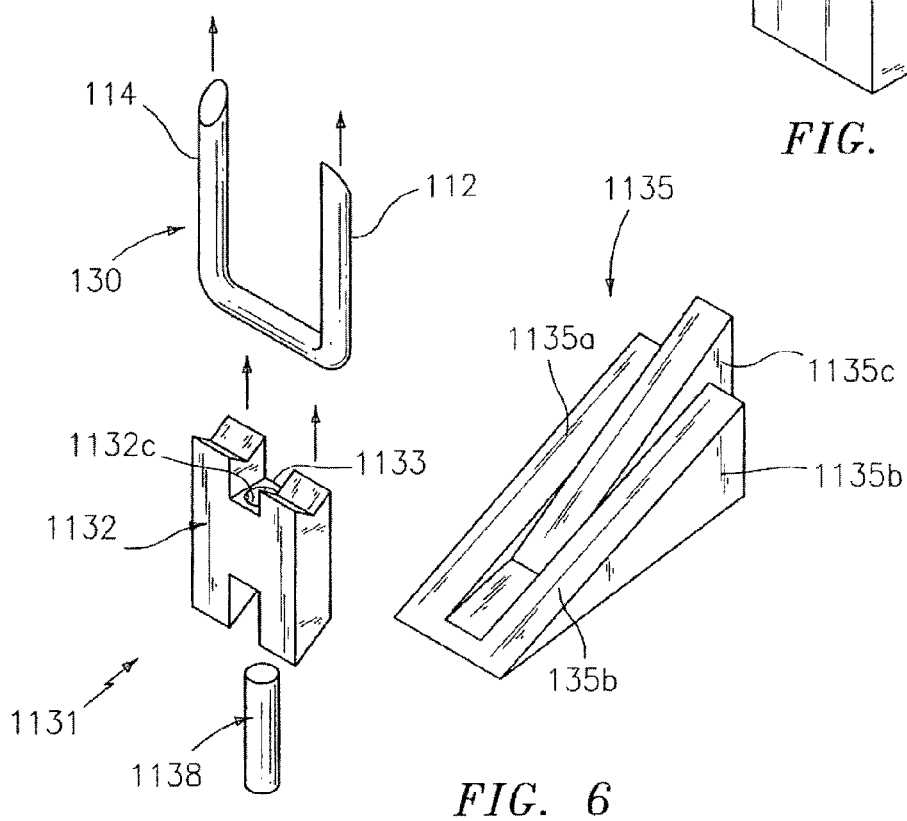
FIG. 6 is a side, perspective view of an actuation structure for a surgical fastening apparatus according to an embodiment of the present disclosure.

The first and second inner wedges, 1135, 1130, that contact the pushers in the first and second inner row of slots, each have wedge surfaces 1135*a* and 1135*b*, defining a crimping wedge surface, and a further dimpling wedge surface 1135*c*. The crimping wedge surface 1135*a* and 1135*b* is disposed on the cam wedge of the sled 1134 so that it is disposed distally of the dimpling wedge surface 1135*c*. The corresponding pusher has a crimping pusher 1132 and a dimpling pusher 1138 that is slidable with respect to the crimping pusher 1132 as shown in FIG. 6. As the sled 1134 is driven distally by the drive bar 107, the crimping wedge surface contacts a crimping pusher 1132 first, driving the surgical fastener against the anvil member 1014. The dimpling wedge surface 1135*c* then comes into contact with the dimpling pusher 1138. The surgical fastener, being still captured between the cartridge and anvil member, is engaged by the dimpling pusher 1138 and a recess 116 is formed in the backspan of the surgical fastener, as shown in FIGS. 3*b* and 5*b*.

As shown in FIG. 6, the dimpling pusher 1138 can be formed as a rod received in a passage 1132*c* in the crimping pusher 1132. The dimpling wedge surface 1135*c* can be formed in the middle of the cam wedge of the sled 1134, with the crimping wedge surface 1135*a* and 1135*b* straddling the dimpling wedge surface. In other embodiments, a crimping wedge surface may be formed on one side of the cam wedge, with the dimpling wedge surface formed on the other side of the cam wedge and the corresponding pusher is arranged accordingly.

The first and second outer wedges, 1133, 1137, that contact the pushers in the first and second outer row of slots, each have a single wedge surface 1139. These wedge surfaces of the first and second outer wedges interact with a corresponding pusher. As the sled 1134 is driven distally by the drive bar 107, the wedge surfaces contact the corresponding pusher, driving the surgical fastener against the anvil member 1014. The anvil member has recesses shaped to deform the surgical fastener to a configuration that is generally closed. For example, the surgical fasteners can be deformed to the B-shaped configuration shown in FIG. 3*a*, the rectangular configuration of FIG. 3*c*, or any other configuration. There is no dimpling of the backspan of the surgical fasteners in the outer rows of slots in the cartridge 100 in this embodiment. In certain preferred embodiments, it is desirable that the surgical fasteners of the inner rows of slots have a smaller interior space, compressing tissue more, than the surgical fasteners of the outer rows of slots.

Figure 5D:
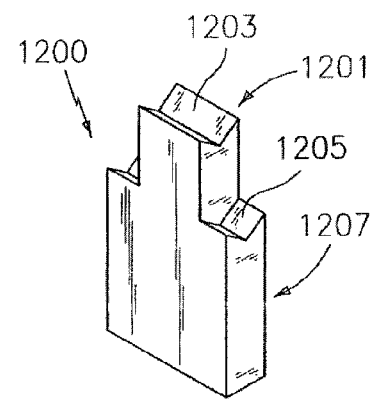
FIG. 5d is a perspective view of a pusher in accordance with an embodiment of the present disclosure.

In a further embodiment, the surgical fastener cartridge has pushers in the inner rows of slots that each has a crimping pusher and a dimpling pusher that are integrally formed, as shown in FIG. 5d. The dimpling pusher 1201 has an upper surface 1203 that extends above an upper surface 1205 of the crimping pusher 1207. As the sled travels through the cartridge distally, the pusher 1200 closes the surgical fastener and forms a recess in the backspan of the surgical fastener at essentially the same time. The wedge of the sled that corresponds to these pushers has a single wedge surface for driving the pusher 1200. The pushers in the outer rows of slots are as discussed above, to form surgical fasteners with a different formed configuration. In certain embodiments, it is desirable that the surgical fasteners of the inner rows of slots have a smaller interior space than the surgical fasteners of the outer rows of slots. The surgical fastener cartridge may have slots arranged transversely or generally perpendicular to the longitudinal axis of the cartridge, or the slots may be generally parallel to the longitudinal axis of the cartridge.

In a further embodiment, the surgical fastener cartridge has pushers with a collapsible portion. After the initial formation of the surgical fastener, the collapsible portion fails. This allows a portion of the pusher to continue to be advanced, forming a dimple or recess in a portion of the backspan of the surgical fastener.

In further embodiments, one or more of the cam wedges are separately actuable by the handle. For example, the handle may include more than one movable handle arm that are each connected to a driving rod. Each movable handle arm can be manipulated by the user to drive a driving rod that interacts with one of the cam wedges. In this way, one or more rows of surgical fasteners can be separately deployed.

In another embodiment, pushers having dimpling pushers are provided at the distal end of a row of surgical fasteners, whereas the remaining pushers in the row do not have dimpling pushers. The surgical fasteners at the distal end of the row have a formed configuration that includes a recess and may have a smaller interior space when formed than the remaining fasteners in the row. In other examples, pushers having dimpling pushers are provided at the proximal end and/or intermediate region of a row of surgical fasteners, whereas the remaining pushers in the row do not have dimpling pushers, to form some surgical fasteners with recesses and relatively smaller interior spaces than the remaining surgical fasteners.

The legs 132 and the backspan 134 of the surgical fasteners may define a cross-section having any suitable geometric configuration, including but not being limited to rectangular, circular oval, square, triangular, trapezoidal, etc. The legs 132 and the backspan 134 may exhibit the same geometrical configuration such that the cross-sectional configuration of the surgical fastener 130 is substantially uniform, as shown in FIG. 2, or alternatively, the legs 132 and the backspan 134 may exhibit different width or geometrical configurations, e.g., the legs 132 may exhibit a rectangular cross-section whereas the backspan 34 may exhibit an oval cross-section.

Prior to the formation of surgical fastener 130, the legs 132 extend from the backspan 134 such that they are substantially parallel. In the alternative, the legs 132 may not extend from the backspan 134 in a parallel arrangement, i.e., the legs 132 may converge or diverge from the backspan. The present disclosure contemplates that the surgical fastener 130 may also be configured as a directionally biased surgical fastener, such as those described in U.S. Pat. No. 7,398,907, the entire contents of which are incorporated by reference herein. The surgical fasteners are formed of a deformable material such as stainless steel, titanium or deformable polymers.

Each of the legs 132 terminates in a penetrating end 136 that is configured to penetrate tissue, e.g., tissue segments "T1", "T2". (See FIG. 3a). The penetrating ends 136 of legs 132 can be tapered to facilitate the penetration of tissue segments "T1", "T2", or alternatively, the penetrating ends 136 may not include a taper. In various embodiments of the surgical fastener 130, the penetrating ends 136 may define a conical or flat surface, as described in co-pending U.S. patent application Ser. No. 11/444,761, published as U.S. Patent Application Publication No. 20060291981, filed Apr. 13, 2003, the entire contents of which are incorporated by reference herein.

In the embodiment of the surgical fastener 130 illustrated in FIG. 2, the backspan 134 is substantially linear in configuration, in the undeformed state. When formed in tissue segments "T1", "T2", the legs 132 of the surgical fastener 130 may be curved toward one another and point toward the backspan, in the shape of the letter "B," as shown in FIG. 3a. The legs 132 cooperate with the backspan 134 to maintain adjacent tissue segments "T1", "T2" in approximation and apply a compressive force "F" thereto. The compressive force "F" applies pressure to the tissue segments "T1", "T2", thereby restricting the flow of blood through the tissue surrounding the surgical fastener 130 and facilitating hemostasis. After formation, the staple has a closed configuration, with an interior space between the backspan 134 and legs 132 that limits the amount of pressure that is applied to the tissue segments "T1", "T2" such that the flow of blood through the tissue is not completely restricted. When formed, the surgical fastener 130 defines an overall height "Hf", measured from the backspan 134 to the outermost curve of the legs 132.

FIGS. 3a, 3b, 3c, and 3d illustrate alternate formed configurations for the fastener. Cartridges and surgical fastening apparatus according to the present disclosure use fasteners that are formed in a combination of one or more formed configurations. The formed configuration of the surgical fasteners can vary from row to row within the cartridge, or can vary within rows within the cartridge. Generally, the surgical fastening apparatus includes actuating structure to form one or more recesses in the backspan of certain surgical fasteners such that the backspan is substantially non-linear in configuration. When formed, the non-linear configuration of the backspan reduces the interior space of the formed surgical fastener and further restricts the flow of blood through the tissue surrounding the surgical fastener, as discussed in further detail below. It may be desirable to apply greater pressure to certain portions of tissue joined by the surgical fastening apparatus, as compared to other portions of tissue, or to account for differences in the thickness of tissue portions engaged by the surgical fastening apparatus.

Figure 3D:
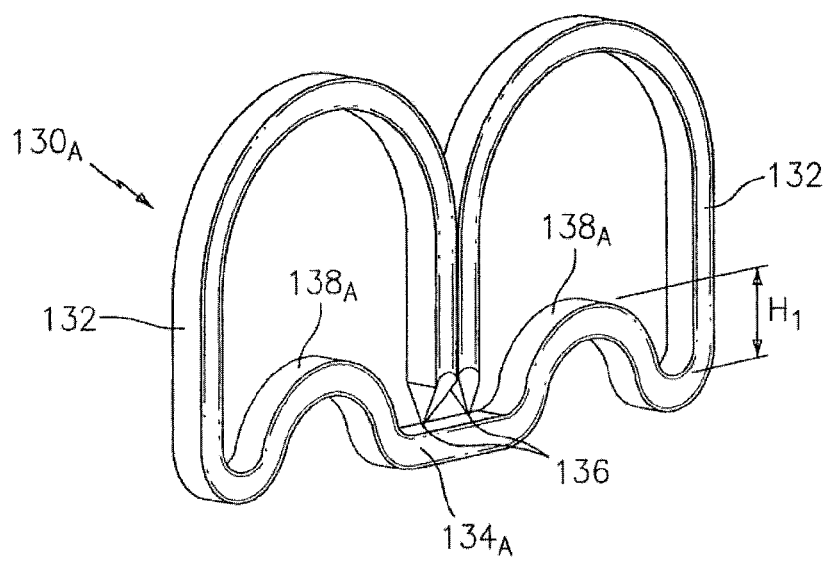
FIG. 3d is a perspective view of a fourth surgical fastener subsequent to formation.

The surgical fastener shown in FIG. 3b has a single recess 116 or hump formed in the backspan of the surgical fastener. By contrast, the surgical fastener shown in FIG. 3c has no recess or hump, and the legs do not have the curved B-shape configuration shown in FIG. 3a. FIG. 3d shows a surgical fastener having two recesses 138A in the backspan of the surgical fastener. The actuation structure will include two dimpling pushers to engage the backspan of the surgical fastener.

Referring to FIG. 3d, a surgical fastener 130a is shown in its formed condition. The surgical fastener 130a includes recesses 138a formed in the backspan 134a that extend inwardly therefrom, curving towards the penetrating ends 136 of the legs 132 and defining a recess or hump of a first height "H1". When the surgical fastener 130a is formed within tissue segments "T1", "T2" the humps/recesses 138a cooperate with the legs 132 of the surgical fastener 130a to apply a compressive force thereto. The compressive force applied by the surgical fastener 130a is greater than the compressive force applied by surgical fastener 130 (FIG. 3a), as the interior space, or compressive space, which is defined between the backspan 134A and the legs 132 and occupied by the tissue segments "T1", "T2" is less in the surgical fastener 130a when compared to the compressive space occupied by the tissue segments "T1", "T2" in the surgical fastener 130 (FIG. 3a). Accordingly, greater pressure is applied to the tissue segments "T1", "T2" by surgical fastener 130a. Consequently, the flow of blood through the tissue surrounding the surgical fastener 130a is more restricted when compared to the flow of blood through the tissue surrounding surgical fastener 130, thereby further facilitating hemostasis. The dimensions of the recesses 138a and the compressive space occupied by the tissue segments "T1", "T2" are such that blood flow is not completely restricted, however, thereby preventing any unnecessary necrosing of tissue. When formed, the surgical fastener 130a may define an overall height "Hf" that is substantially equal to that defined by the surgical fastener 130.

In a further example, the recesses or humps formed in the backspan of the staples can be varied to vary the interior space or compressive space of the formed staple, to compress certain portions of tissue more as compared to other portions of tissue joined by the surgical fastening apparatus. In an embodiment, for example, the surgical fastener cartridge forms surgical fasteners with smaller recesses in the first and second outer rows of slots and surgical fasteners with comparatively larger recesses in the first and second inner rows of slots. Accordingly, when the surgical fastener is formed within tissue segments "T1", "T2", the recesses cooperate with the legs of the surgical fastener to apply a compressive force thereto. The compressive force applied by the surgical fastener with the larger recesses is greater than the compressive forces applied by the surgical fasteners with the smaller recesses, as the compressive space occupied by the tissue segments "T1", "T2" is less. When formed, the surgical fasteners define an overall height "Hp" that that may be substantially equal.

In the embodiment shown in FIG. 1, the surgical fasteners installed within the cartridge body 112 are arranged to define a pair of inner rows and a pair of outer rows that correspond to the respective inner and outer rows of fastener retention slots 126 formed in the top wall 120. Accordingly, the pair of inner rows are spaced laterally from the longitudinal slot 122, on opposite sides thereof, and the pair of outer rows are spaced laterally from the pair of inner rows, again on opposite sides of the longitudinal slot 122 such that the surgical fasteners will be deployed on opposite sides of the cut-line (not shown) created in the tissue upon fastening. That is, the fasteners with the recesses 116 (FIG. 3b) provide a greater compressive force as there is a shorter distance between the curve (hump) of the recess and the curve of the formed legs, the fasteners have a smaller interior space, and in the illustrated embodiment these fasteners are provided in the inner rows closer to the cut line. The fasteners with a greater distance between the curve of the legs and the backspan and are provided on the outer rows. If a third row of fasteners is used in this embodiment, then the fasteners with the smallest interior space (such as, for example, fasteners with relatively large recesses) would preferably be placed on the innermost rows closest to the cut line. By providing the rows of fasteners which provide greater tissue compression as you approach the cut line, tissue is compressed more adjacent the cut line. It should be appreciated however, that the fasteners can be placed in other arrangements in the rows than the foregoing arrangement. Also, the present disclosure contemplates the use of any of the surgical fasteners disclosed herein such that a surgical fastener with only a single formed configuration, e.g., surgical fastener 130, is present, or surgical fasteners with a variety of formed configurations are used.

Figure 8:
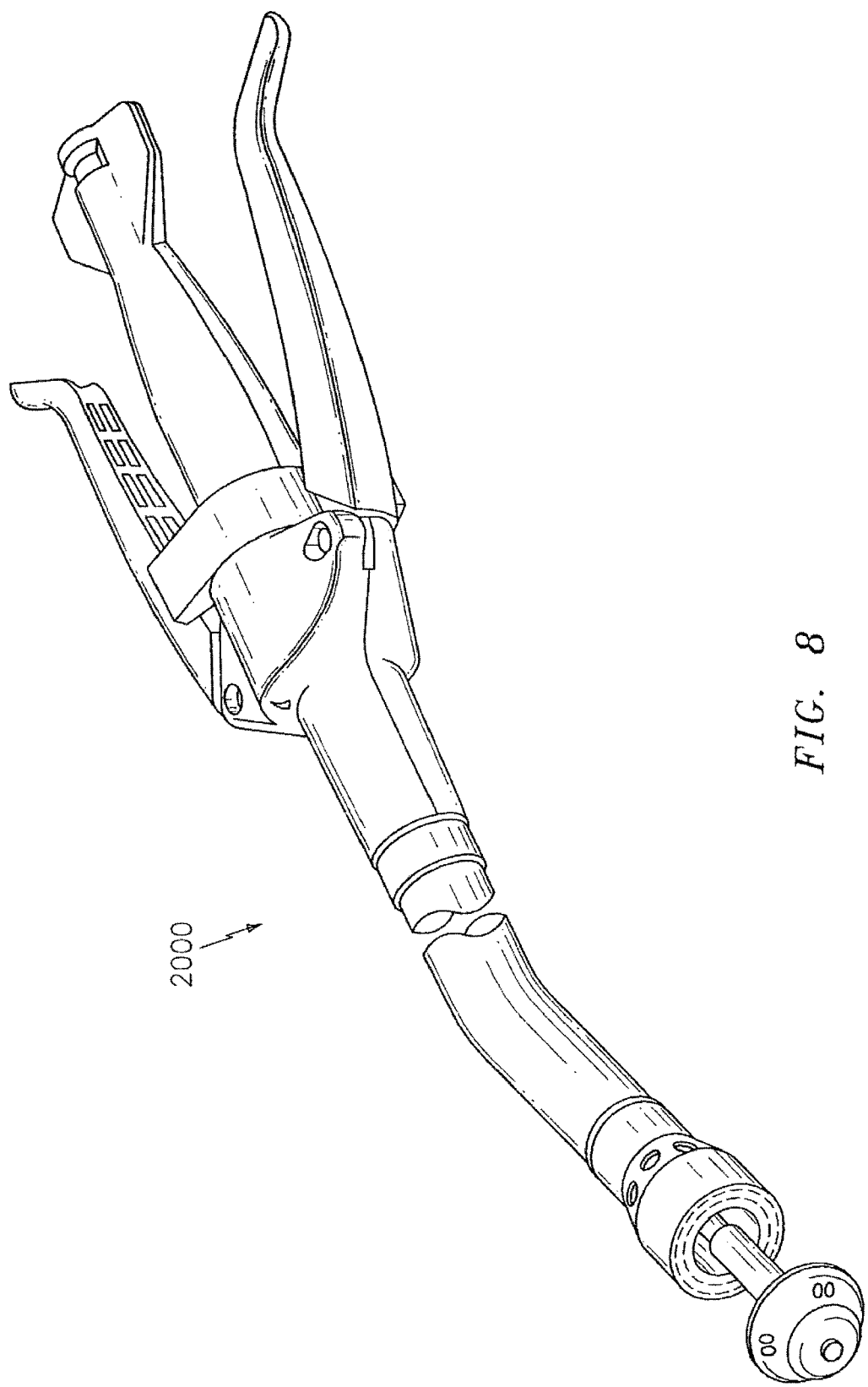
FIG. 8 is a perspective view of surgical fastener applying apparatus in accordance with an embodiment of the present disclosure.
Figure 9:
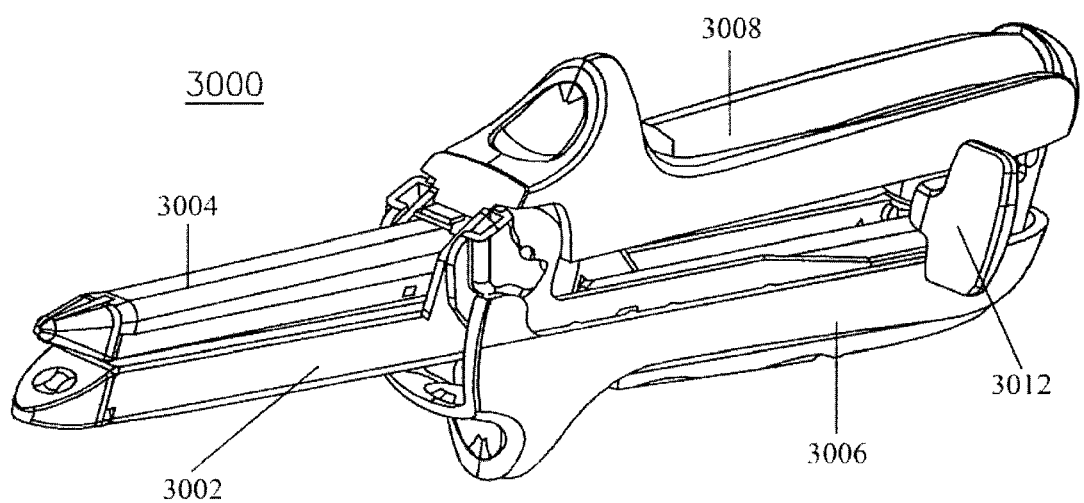
FIG. 9 is a perspective view of a surgical fastener applying instrument in accordance with an embodiment of the present disclosure.

While surgical fastener applying apparatus 1000 is depicted as an apparatus suitable for use in laparoscopic procedures for performing surgical anastomotic fastening of tissue, it should be understood that surgical fastener cartridge 100 may be adapted for use with any surgical instrument suitable for the intended purpose of applying surgical fasteners to tissue. For example, surgical fastener cartridge 100 may be adapted for use with an end-to-end anastomosis device 2000, as seen in FIG. 8, a surgical fastener applying instrument 3000, as seen in FIG. 9, for use during an open gastrointestinal anastomotic fastening procedure, or any of the surgical fastener applying apparatus discussed in U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, which are each incorporated by reference herein in their entirety.

The surgical stapling apparatus 3000 includes a cartridge receiving half-section 3002, which accommodates a plurality of surgical fasteners, and an anvil half-section 3004. The half-sections 3002, 3004 are pivotally connected via handles 3006, 3008 for approximation during use. Following approximation of the half-sections 3002, 3004, the surgical fastener applying apparatus 3000 is fired by driving a firing slide distally through the advancement of a firing lever 3012. Distal movement of the firing slide causes a plurality of cam bars to engage camming surfaces that interact with a plurality of pushers to expel the plurality of surgical fasteners from the cartridge receiving half-section 3002. The surgical fasteners are positioned on either side of a track which guides a knife during longitudinal movement to thereby sever tissue along a cut-line.

Figure 10:
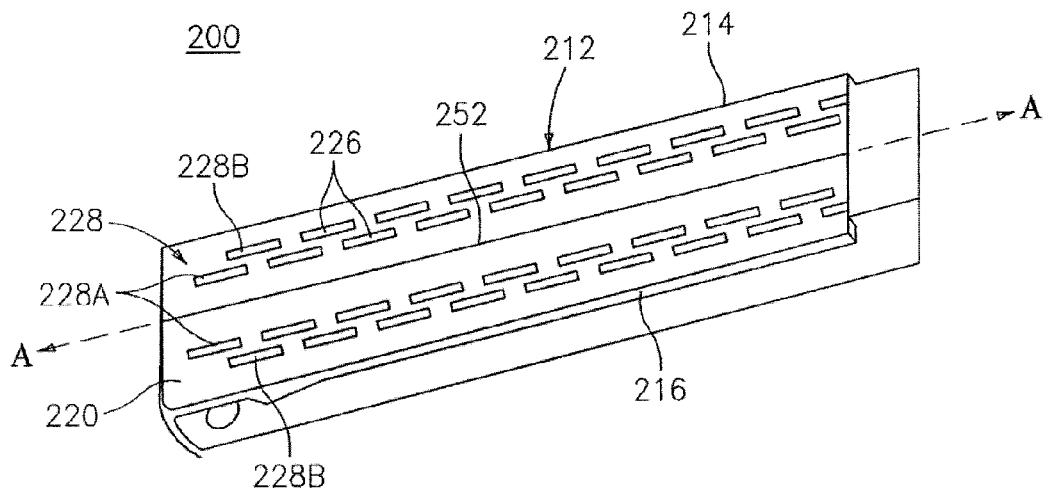
FIG. 10 is a perspective view of a cartridge for a surgical fastener applying instrument in accordance with an embodiment of the present disclosure.

Referring now to FIG. 10, in an alternate embodiment, a surgical fastener cartridge 200 is disclosed. Surgical fastener cartridge 200 is similar to surgical fastener cartridge 100 in that it contains rows of fasteners, however it does not have a longitudinal slot 122 (FIG. 1) configured to accommodate a knife or other cutting element (although in alternate embodiments, a knife could be provided). As with surgical fastener cartridge 100, surgical fastener cartridge 200 includes a plurality of fastener retention slots 226 on a top wall 220 of cartridge body 212 that are arranged into a plurality of rows 228. The rows 228 of retention slots 226 are spaced laterally from a centerline 252 extending along the longitudinal axis "A-A" defined by cartridge body 212 and preferably spaced equidistant from sidewalls 214, 216. As shown, the plurality of rows 228 includes a pair of first (inner) rows 228a disposed on opposite sides of centerline 252 and a pair of second (outer) rows 228b spaced laterally from the pair of first rows 228a, again on opposite sides of the centerline 252. Each of the slots extend generally parallel to the longitudinal axis. Each of the fastener retention slots 226 is configured to receive one of a plurality of surgical fasteners and pushers (not shown) such that the surgical fasteners are deployed in rows, e.g., inner and outer rows in the embodiment of FIG. 18, on opposite sides of the centerline 252 and formed into fasteners having one or more formed configurations, e.g., surgical fasteners shown in FIGS. 3a, 3b, 3c, 3d.

Figure 4:
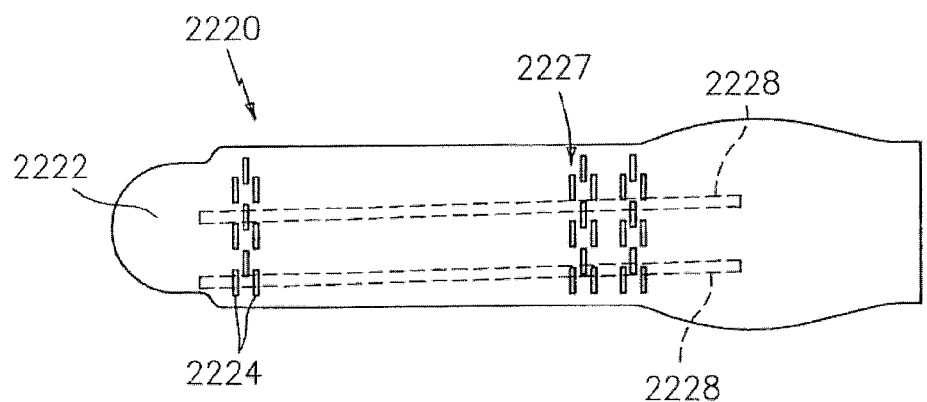
FIG. 4 is a plan view of a surgical fastener cartridge for a surgical fastening apparatus according to an embodiment of the present disclosure.

FIG. 4 shows an example of a surgical fastener cartridge 2220 having slots 2224, formed in the upper surface 2222 of the cartridge. The slots extend generally perpendicularly to the longitudinal axis. These slots 2224 are arranged in columns, such as column 2227 and rows 2228. This cartridge 2220 does not include a longitudinal slot for a knife. The cartridge 2220 includes a plurality of pushers as discussed herein for forming certain of the fasteners with a relatively large interior space, and other fasteners with a relatively small interior space.

Although the surgical fastener cartridge 200 of FIG. 10 is depicted as including pairs of first and second rows 228a, 228b, respectively, additional rows of fastener retention slots 226, and accordingly, additional rows of surgical fasteners, may be included in alternate embodiments of the surgical fastener cartridge 200, as discussed above with respect to surgical fastener cartridge 100. Also, the fasteners may be arranged in differing fashions within the cartridge as discussed herein with respect to the other cartridge embodiments.

Figure 11:
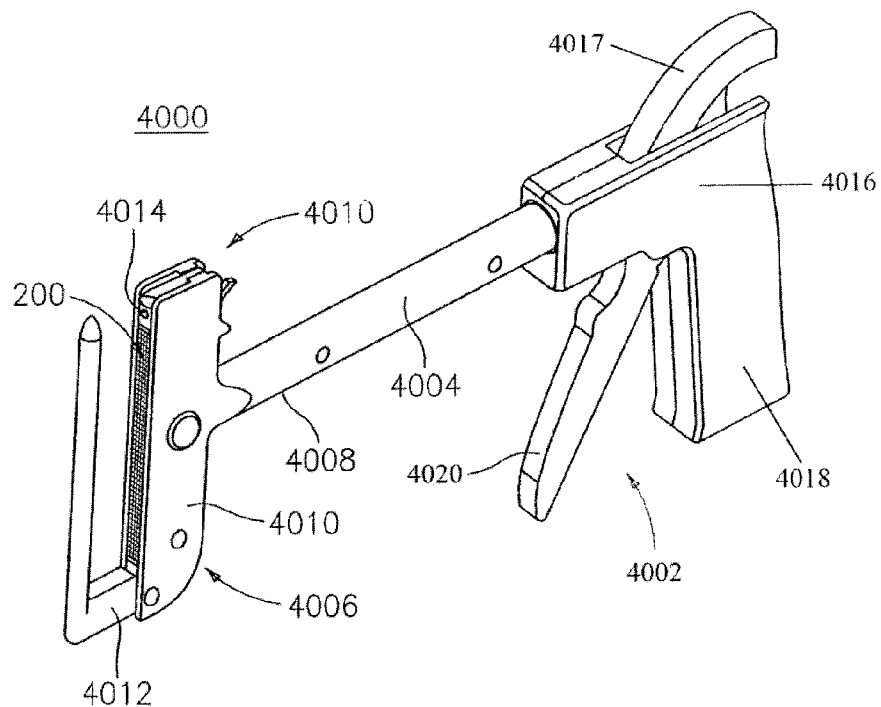
FIG. 11 is a perspective view of a surgical fastener applying instrument in accordance with an embodiment of the present disclosure.

With additional reference to FIG. 11, a surgical fastener applying apparatus 4000 of either the re-usable or disposable variety is illustrated for use with the surgical fastener cartridge 200. Surgical fastener applying apparatus 4000 includes a handle assembly 4002, an elongated portion 4004 extending distally from the handle 4002, and an arm 4006 extending from a distal end 4008 of the elongated portion 4004. The surgical fastener applying apparatus 4000 further includes an end effector 4010 including an anvil 4012 orthogonally affixed to arm 4006 and a surgical fastener cartridge receiver 4014 operatively coupled to the distal end 4008 of elongated portion 4004 for holding the surgical fastener cartridge 200 thereon.

In operation, surgical fastener applying apparatus 4000 is fired similarly to and in accordance with other known surgical stapling instruments. For a detailed discussion of the approximation and firing of surgical stapling instrument 4000, reference is made to commonly assigned U.S. Pat. No. 5,964,394, currently assigned to Tyco Healthcare Group LP, the entire contents of which is incorporated herein by reference. The handle assembly 4002 includes a housing 4016, which includes a stationary handle member 4018. A movable handle 4020 is pivotably supported within the housing 4016 and is biased away from the stationary handle member 4018. Movement of the movable handle member 4020 in the direction of the stationary handle member 4018 imparts a driving force to an actuation shaft within the housing 4016 which in turn imparts a force to a pusher bar within the staple cartridge 4014 to thereby eject fasteners disposed within slots of the staple cartridge 200 and to drive the surgical fasteners against a staple forming surface of the anvil member 4012. Prior to advancing the staple cartridge 4014 towards the anvil 4012, the physician moves an approximation lever 4017 towards the housing 4016 which causes the staple cartridge 4014 to move towards anvil 4012 prior to firing the staples and approximating the staple cartridge 4014 relative to the anvil 4012 with tissue disposed therebetween.

Surgical fastener applying apparatus 4000 is used to apply a plurality of surgical fasteners, e.g., surgical fasteners 130 to either side of a target section of tissue (not shown), and may be any surgical fastener applying apparatus suitable for this intended purpose, including but not being limited to the transverse anastomosis fastening instrument disclosed in U.S. Pat. No. 7,070,083, the entire contents of which having been previously incorporated by reference herein. The fastener applying apparatus has a plurality of pushers that are advanced in the distal direction to deploy the surgical fasteners from the cartridge, in the distal direction, against the anvil. The surgical fasteners are generally deployed and formed simultaneously. To form surgical fasteners with different formed configurations (e.g., as shown in FIGS. 3a, 3b, 3c, 3d) as compared to other surgical fasteners in the cartridge, some of the pushers have a dimpling pusher and a crimping pusher. The dimpling pusher and crimping pusher may be movable with respect to one another, to separately close the surgical fastener and then form a recess in the backspan of the surgical fastener, or the dimpling pusher and crimping pusher may be integrally formed with one another. Thereafter, a scalpel or other such cutting element may be used to remove the target section of tissue. Further details regarding the use and function of surgical fastener applying apparatus 4000 may be obtained through reference to U.S. Pat. No. 7,070,083. In an alternate embodiment, the apparatus 4000 could include a cutting element as in the other cartridges disclosed herein.

The surgical fastener applying apparatus according to certain embodiments of the present disclosure include a plurality of cam bars for interacting with the pushers to deploy the surgical fasteners. For example, the apparatus disclosed in U.S. Pat. No. 5,318,221, the disclosure of which is hereby incorporated by reference herein, in its entirety, has a cam bar adapter that holds a plurality of cam bars and a knife. A channel is advanced through operation of the handle of the apparatus, which drives the cam bars and knife forward. A clamp tube that surrounds the proximal end of the anvil is advanced to clamp the anvil and cartridge together. In another example, the apparatus disclosed in U.S. Pat. No. 5,782,396, the disclosure of which is hereby incorporated by reference herein, in its entirety, has an actuation sled. An elongated drive beam is advanced distally through operation of the handle of the apparatus, driving the actuation sled forward. The distal end of the drive beam engages the anvil and the channel that support the cartridge as the drive beam travels distally, to deploy the staples and clamp the anvil and cartridge together.

The present disclosure contemplates a surgical stapling apparatus having a surgical fastener cartridge with an upper surface defining a plurality of slots, the slots being arranged in a first inner row and a first outer row, each slot in the first inner row containing a first inner surgical fastener and a pusher having a crimping pusher and a dimpling pusher arranged to form the first inner surgical fastener in a first closed configuration and to form a recess in a backspan of the surgical fastener, each slot in the first outer row containing a first outer surgical fastener and a pusher arranged to form the first outer surgical fastener in a second formed configuration.

The present disclosure further contemplates a surgical stapling apparatus having a surgical fastener cartridge with an upper surface defining a plurality of slots, the slots being arranged in a first inner row and a first outer row, each slot in the first inner row containing a first inner surgical fastener and a pusher arranged to form the first inner surgical fastener so that the formed first inner surgical fastener has a first interior space and a backspan that is deformed, each slot in the first outer row containing a first outer surgical fastener and a pusher arranged to form the first outer surgical fastener so that the formed first outer surgical fastener has a second interior space, the first interior space being smaller than the second interior space.

It should be understood that the present disclosure is not limited to the precise embodiments discussed herein above, and that various other changes and modifications may be contemplated by one skilled in the art without departing from the scope or spirit of the present disclosure. For example, the surgical fasteners described herein above may be formed from a variety of surgically acceptable materials including titanium, plastics, bio-absorbable materials, etc. Although the illustrative embodiments of the present disclosure have been described herein with reference to the accompanying drawings, the above description, disclosure, and figures should not be construed as limiting, but merely as exemplary of various embodiments.

What is claimed is:

1. A surgical fastener applying apparatus comprising:
    a fastener assembly including an anvil section and a cartridge section, at least one of the cartridge section and the anvil section being movable from an unclamped position to a clamped position to clamp tissue therebetween, the cartridge section having a tissue contacting surface with a plurality of retention slots formed therein, the cartridge section and anvil section defining a longitudinal axis, the plurality of retention slots having an elongate shape and extending transversely with respect to the longitudinal axis;
    a plurality of first surgical fasteners and a plurality of second surgical fasteners retained within the cartridge section, each surgical fastener disposed within a corresponding retention slot;
    a plurality of first pushers and a plurality of second pushers positioned within the cartridge section, the first pushers corresponding to the first surgical fasteners and the second pushers corresponding to the second surgical fasteners, at least one of the first pushers and second pushers being arranged to form a recess in a backspan of at least one of the first surgical fasteners and second surgical fasteners; and
    an actuation member movable through the cartridge section and engagable with the plurality of first pushers and the plurality of second pushers.

2. The surgical fastener applying apparatus according to claim 1, wherein the plurality of first pushers are configured and dimensioned to deform the first surgical fasteners from an initial configuration into a subsequent configuration the plurality of second pushers being configured and dimensioned to deform the second surgical fasteners from an initial configuration into a subsequent configuration.

3. The surgical fastener applying apparatus according to claim 2, wherein the first surgical fasteners and second surgical fasteners have backspans, at least some of the first pushers and second pushers deforming the backspans of the respective surgical fasteners.

4. The surgical fastener applying apparatus according to claim 1, wherein the plurality of first pushers are configured and dimensioned to form a first recess in a backspan of at least one of the plurality of first surgical fasteners.

5. The surgical fastener applying apparatus according to claim 4, wherein the plurality of second pushers are configured and dimensioned to form a second recess in a backspan of at least one of the plurality of second surgical fasteners to define the subsequent configuration.

6. The surgical fastener applying apparatus according to claim 1, wherein the plurality of first pushers are configured, dimensioned, and positioned to deform the plurality of first surgical fasteners upon engagement of the plurality of first surgical fasteners with the anvil section, and the plurality of second pushers are configured, dimensioned, and positioned to deform the plurality of second surgical fasteners upon engagement of the plurality of second surgical fasteners with the anvil section.

7. The surgical fastener applying apparatus according to claim 1, wherein the cartridge section includes a first inner row of retention slots and a first outer row of retention slots.

8. The surgical instrument according to claim 1, wherein the plurality of first pushers and the plurality of second pushers each include a first pusher element and a second pusher element.

9. The surgical instrument according to claim 8, wherein the first pusher element is configured and dimensioned to receive the second pusher element such that the second pusher element is movable through the first pusher element.

10. The surgical fastener applying apparatus according to claim 9, wherein the second pusher element forms a recess in a backspan of a respective surgical fastener.

\* \* \* \* \*